(12) United States Patent
Schmid

(10) Patent No.: US 7,514,090 B2
(45) Date of Patent: Apr. 7, 2009

(54) MONOCYTE LOCOMOTION INHIBITORY FACTOR

(75) Inventor: Roberto Rodolfo Kretschmer Schmid, Pedregal (MX)

(73) Assignee: The Center for Blood Research, Boston, MA (US)

(*) Notice: Subject to any disclaimer, the term of this patent is extended or adjusted under 35 U.S.C. 154(b) by 620 days.

(21) Appl. No.: 10/861,123

(22) Filed: Jun. 4, 2004

(65) Prior Publication Data

US 2004/0259807 A1   Dec. 23, 2004

Related U.S. Application Data

(63) Continuation-in-part of application No. 10/263,947, filed on Oct. 3, 2002, now Pat. No. 7,078,044, which is a continuation of application No. 09/342,956, filed on Jun. 29, 1999, now Pat. No. 6,524,591.

(30) Foreign Application Priority Data

Jun. 29, 1998   (MX) ..................................... 985265

(51) Int. Cl.
*A61K 39/05* (2006.01)
*C07K 5/00* (2006.01)

(52) U.S. Cl. .................. 424/269.1; 424/9.1; 424/9.2; 424/265.1; 530/300

(58) Field of Classification Search .................. None
See application file for complete search history.

(56) References Cited

U.S. PATENT DOCUMENTS 6,524,591 B1 *   2/2003   Schmid ................... 424/265.1
7,078,044 B2 *   7/2006   Schmid ................... 424/269.1

FOREIGN PATENT DOCUMENTS

WO    WO94/03487   *   2/1994

OTHER PUBLICATIONS

McConchie et al. Infection and Immunity, 2006, vol. 74, pp. 6632-6641.*
Rahman et al. PloS Pathogens, 2006, vol. 2, pp. 0066-0077.*
Rico, et al., Production of the Monocyte Locomotion Inhibitory Factory (MLIF) By Axenically Grown *Entamoeba Histoloytica*: Synthesis or Degradation? Archives of Medical Research 28:S235-S236 (1997).
Kretschmer, et al., "Inhibition of human monocyte locomotion by products of axenically grown *E. histolytica*," *Parasite Immunology*, 1985, pp. 527-543.
Rico et al., The Monocyte Locomotion Inhibitory Factor (MLIF) Produced by Axenically Grown *Entamoeba histolytica* Fails to Affect the Locomotion and the Respiratory Burst of Human Eosinophils In Vitro, *Archives of Medical Research*, vol. 28, Suppl., pp. S233-S234, 1997.
Kretschmer, et al., "The role of mannose in the receptor of the monocyte locomotion ;Inhibitory Factor Produced by Axenically Grown *Entamoeba histolytica*," *Parasitology Research* (1989) 75:245-246.
Rico et al., "Cyclic Nucleotide Changes Induced in Human Leukocytes by a Product of Axenically Grown *Entamoeba histolytica* that Inhibits Human Monocyte Locomotion" *Parasitology Research* (1995) 81:158-162.
Scherer et al., "Inhibition of Contact Cutaneous Delayed Hypersensitivity Reactions to DNBc in Guinea Pigs by the Monocyte Locomotion Inhibitory Factor (MLIF) Produced by Axenically Grown *Entamoeba histolytica*," *Archives of Medical Research*, vol. 28, Suppl., pp. S237-S238, 1997.

* cited by examiner

*Primary Examiner*—Bruce Campell
*Assistant Examiner*—Agnieszka Boesen
(74) *Attorney, Agent, or Firm*—Rissman Hendricks & Oliverio LLP

(57) ABSTRACT

The invention relates to an anti-inflammatory oligopeptides which contain the terminal pharmacophore Cys-Asn-Ser which is capable of inhibiting the NF-κβ signaling pathway. The oligopeptides are useful in stimulating the in vivo production of IL-10, and for treating inflammatory diseases and scarring when formulated in pharmaceutical compositions for administration to patients.

12 Claims, 2 Drawing Sheets

SEQUENCE LISTING

```
<160> NUMBER OF SEQ ID NOS: 1

<210> SEQ ID NO 1
<211> LENGTH: 5
<212> TYPE: PRT
<213> ORGANISM: E. histolytica
<220> FEATURE:
<221> NAME/KEY: PEPTIDE
<222> LOCATION: (1)..(5)

<400> SEQUENCE: 1

Met Gln Cys Asn Ser
1               5
```

MONOCYTE LOCOMOTION INHIBITORY FACTOR

CROSS-REFERENCE TO RELATED APPLICATIONS

This application is a continuation-in-part of U.S. application Ser. No. 10/263,947, filed Oct. 3, 2002 now U.S. Pat. No. 7,078,044, which is a continuation of U.S. application Ser. No. 09/342,956, filed Jun. 29, 1999, now U.S. Pat. No. 6,524,591. The pertinent portions of the above-identified applications and patents are incorporated herein by reference in their entirety.

BACKGROUND OF THE INVENTION

The invention relates to the further characterization of the structure and function of the isolated oligopeptide obtained from *Entamoeba histolytica*, previously identified as monocyte locomotion inhibitory factor ("MLIF"). This characterization has led to the discovery of a family of oligopeptides useful for the treatment of a variety of inflammatory conditions, such as rheumatoid arthritis and psoriasis.

*Entamoeba histolytica*, in motile form, is a dynamic pleomorphic protozoon which is common in Mexico, Africa and Asia. *E. histolytica* is an invasive parasite having a simple cytoplastic structure. Infection by pathogenic *E. histolytica* may result in the invasion of several organs and tissues in humans. The most commonly affected organs are the colon and the liver. Less frequently, the parasite may invade the lungs, the brain, the skin and the genitalia.

*E. histolytica* is known to cause liver abscesses and other lesions in the human population. In amoebic liver lesions, a moderate inflammation occurs characterized by the presence of neutrophils, epithelioid cells and macrophages, with less abundant neutrophils, lymphocytes and plasma cells. It has been observed that although the early stages of parasitic invasion are characterized by acute inflammation in which even some eosinophilic leukocytes occur, the advanced stages are characterized by a scarcity of inflammation. Moreover, livers with such hepatic abscesses have been found to regenerate perfectly without a trace of scarring following effective treatment with appropriate medicines. Sepulveda, B. et al., *Immunology of Parasitic Disease*, ppg. 170-191 (1982).

The supernatant fluid of axenically grown *E. histolytica* has been shown to inhibit chemotaxis, chemokinesis and the random mobility of human mononuclear phagocytes. Human polymorphonuclear neutrophil phagocyte locomotion is apparently unaffected. It has been postulated that the inhibition of human mononuclear phagocytes by the entamoeba product contributes to the lack of inflammatory reaction observed in the advanced stages of invasive amoebiasis, and consequently and auspiciously, to the lack of scar tissue formation upon healing of amoebic lesions through regeneration. Kretschmer, R. R. et al., Parasite Immunology, 7, Pages 527-543 (1985). See also Rico, G. et al., Archives of Medical Research, 28(5), pages 235-236 (1997). This product may also constitute a defensive factor of the amoeba which is capable of reducing or blocking the inflammatory response of the host.

In basic terms, inflammation is a localized, protective response elicited by a foreign antigen, or by an injury or destruction of tissue. Inflammation occurs when tissues are injured by viruses, bacteria, trauma, chemicals, heat, cold, or any other harmful stimuli. In such instances, the classic weapons of the immune system (T cells, B cells, macrophages) interface with cells and soluble products which are mediators of inflammatory responses (neutrophils, eosinophils, basophils, macrophages, cytokines, kinin and coagulation systems, and the complement cascade).

A typical inflammatory response is characterized by (i) migration of leukocytes at the site of the injury or trauma; (ii) specific and nonspecific recognition of foreign antigens mediated by B and T lymphocytes, macrophages and the alternative complement pathway; (iii) amplification of the inflammatory response with the recruitment of specific and nonspecific effector cells by complement components, lymphokines and monokines, kinines, arachidonic acid metabolites, and mast cell/basophil products; and (iv) macrophage, neutrophil and lymphocyte participation in antigen destruction, with the ultimate removal of antigen particles or injured tissue by phagocytosis. Diseases associated with such inflammatory responses include rheumatoid arthritis, lupus and psoriasis. The rejection of allografts following organ transplantation also involves these inflammatory responses.

NF-κβ protein is a transcription factor that is activated by pro-inflammatory signals. The NF-κβ signaling pathway is a conserved evolutionary system that is essential for host defense. The system triggers and regulates innate immunity, and co-signals adaptive immunity in humans. The members of the NF-κβ system form homodimers and heterodimers (p50/p50 and p50/p65) which, when linked to natural upstream NF-κβ inhibitors, such as Iκβ's, fail to translocate to the nucleus. When the Iκβ's are degraded in the proteosome, the NF-κβ homodimers and heterodimers are set free to translocate into the nucleus and to start the transcription of many critical genes. See FIG. 1 below. NF-κβ p65/p50 heterodimers are the leading gene transcriptors, while p50/p50 homodimers act as inhibitors.

Although inflammation is an essential defense mechanism against infection, it is nevertheless appropriate to consider approaches to modulate or directly inhibit the inflammation if failure to do so would lead to severe and irreversible damage to organs and tissue, including scarring.

It will therefore be readily appreciated that a continuing need exists to develop improved treatments for inflammatory diseases, as well as treatments for conditions of moderate and extreme inflammation.

SUMMARY OF THE INVENTION

This invention relates to a new family of oligopeptides having, as the terminal pharmacophore group thereof, the amino acids Cys-Asn-Ser, and to the use of such oligopeptides as potent inhibitors of the NF-κβ signaling pathway. In one aspect of this invention, the oligopeptide is the three amino acid protein Cys-Asn-Ser.

The invention also relates to the in vivo inhibition of the NF-κβ signaling pathway in a subject, leading, in turn, to the inhibition of pro-inflammatory cytokines such as IL-1β and IL-6. In one aspect of this embodiment, the NF-κβ signaling pathway is disrupted by inhibiting the syntesis of the MyD88 coupling protein in cells, such as human monocyte cells, resulting in membrane translocation. Oligopepitdes that are effective to inhibit NF-κβ include those oligopeptides having the terminal pharmacophore group Cys-Asn-Ser, such as MLIF (Met-Gln-Cys-Asn-Ser; SEQ ID NO:1), which is produced by the parasitic organism *Entamoeba Histolytica*.

In another embodiment, the present invention relates to the in vivo generation of the anti-inflammatory cytokine IL-10 by the administration to a subject of a pharmaceutical composition comprising an oligopeptide having the terminal pharmacophore group Cys-Asn-Ser.

In yet another embodiment of the invention, a pharmaceutical composition comprising the oligopeptides of this invention is administered to a subject to prevent scarring resulting from an inflammatory process mediated by leukocytes. The oligopeptide-based compositions of this invention are capable of inhibiting the activity and mobility of leukocyte macrophages, thereby inhibiting late stage inflammation, as well as blocking the fibroblast growth factor signaling adaptor, thereby blocking the expression of this protein.

These and other aspects of the invention are described in greater detail below.

DETAILED DESCRIPTION OF THE INVENTION

Figure 1:
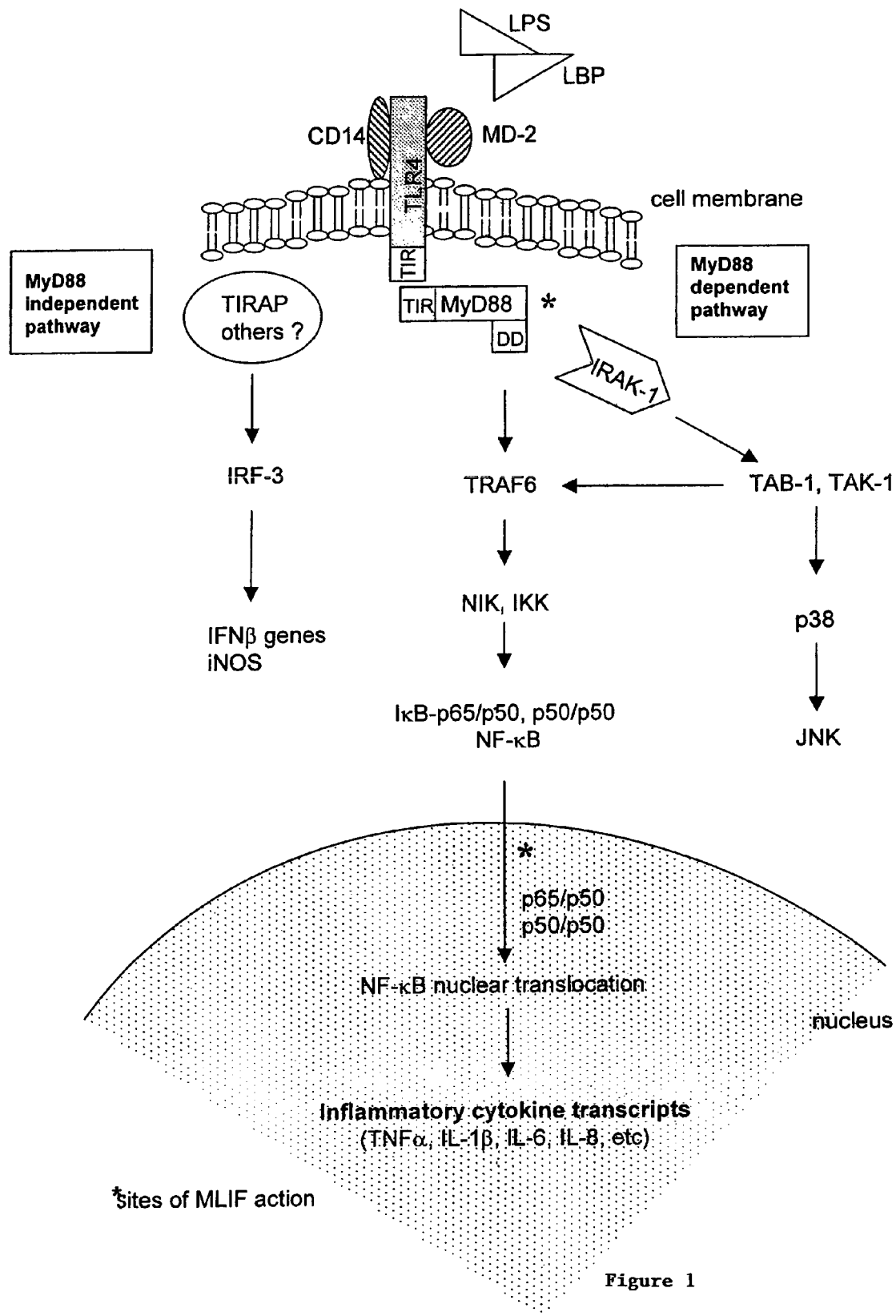
FIG. 1 is a diagram showing the NF-κβ signaling pathway and the complementary MyD88 pathway. The sites of action of MLIF in these pathways are noted.

The invention relates to compositions comprising oligopeptides which are capable of reducing the effects of inflammation in a subject due to an inflammatory condition, such as a condition resulting from rheumatoid arthritis or organ transplantation. Administration of the compositions of the invention selectively inhibits the activity and mobility of certain leukocytes, i.e., monocytes, and also inhibits the metabolism of both monocytes and neutrophils, in the vicinity of the inflammation, without affecting these functions in other cells, i.e, eosinophils.

As used herein, the expression "monocyte locomotion inhibitory factor" (MLIF) means the oligopeptide isolated from the supernatant fluid of axenically grown *E. hislolylica*. Also as used herein, an "isolated" peptide means a peptide that is not in its natural state (e.g., it is dissociated from a larger protein molecule in which it naturally occurs), or a non-naturally occurring fragment of a naturally occurring protein, or a peptide dissociated from other cell components with which it is associated in its natural state. Isolated also may mean that the amino acid sequence of the peptide does not occur in nature, for example, because the sequence is modified from a naturally occurring sequence, or because the sequence does not contain flanking amino acids which are present in nature.

An isolated peptide can be purified from a biological extract, prepared in vitro by recombinant or synthetic means, and/or modified by attachment of a moiety (e.g., a fluorescent, radioactive, or enzymatic label, or an unrelated sequence of amino acids to make a fusion protein) which does not correspond to a portion of the peptide in its native state. Isolated peptides include chimeric proteins comprising a fusion of an isolated peptide with another peptide, e.g., a peptide capable of targeting the isolated peptide to a cell type or tissue type, enhancing stability of the isolated peptide under assay conditions, or providing a detectable moiety, such as green fluorescent protein. A moiety fused to an isolated peptide or a fragment thereof also may provide a means of readily detecting the fusion protein, e.g., by immunological recognition or by fluorescent labeling. Purified isolated peptides include peptides isolated by methods including, but not limited to, immunochromotography, HPLC, size-exclusion chromatography, ion-exchange chromatography and immune-affinity chromatography.

The oligopeptides of this invention include those oligopeptides having the terminal pharmacophore group Cys-Asn-Ser, as well as the isolated three amino acid peptide Cys-Asn-Ser. The oligopeptides of this invention are capable of inhibiting the NF-κβ signaling pathway by disrupting the membrane-related MyD88 recruitment pathway in cells, such as human monocyte cells. These oligopeptides can be formulated into compositions for the treatment of inflammatory disorders and scarring as described in more detail herein. The terms "inhibitor" or "inhibitory substance" as used herein broadly include substances which are effective to inhibit, or block the level of expression of, the particular molecule or cytokine on fibroblast cells at the site of the potential adhesion. Suitable inhibitory substances include, inter alia, substances effective to inhibit activity at the gene transcription level, such as oligonucleotides that bind to the gene promoter region. Inhibitors which function at the gene level by a transcriptional mechanism generally involve the use of specific proteins and/or agents that bind to promoter regions of the gene, and prevent trans-acting elements from enhancing the transcription of the gene. Activation of the transcription factor NF-κβ is required for the coordinate expression of IL-1β and IL-6 genes, and possibly other factors which are ingredients of the inflammatory reaction.

The amino acid sequence of the oligopeptides of this invention may be of natural or non-natural origin, that is, the oligopeptide molecule may comprise a natural peptide molecule that is a piece of a naturally occurring molecule, it may comprise a sequence modified from a naturally occurring molecule, or it may be entirely synthetic so long as the peptide has the ability to inhibit the NF-κβ signaling pathway.

The oligopeptides of the invention also may be altered versions of the foregoing oligopeptides. For example, oligopeptides in this context may be fusion proteins of the oligopeptides and unrelated amino acids, synthetic peptides of amino acids, labeled peptides, or peptides coupled to nonpeptide molecules (for example in certain drug delivery systems).

Nonpeptide analogues of peptides, e.g., those which provide a more stabilized structure, or altered biodegradation, or which can act at lower concentrations, are also contemplated. Peptide mimetic analogues can be prepared based on a selected peptide by replacement of one or more residues with nonpeptide moieties. Preferably, the nonpeptide moieties permit the peptide to retain its natural conformation, or stabilize a preferred conformation. One example of methods for preparing nonpeptide mimetic analogues from peptides is described in Nachman et al., Regul. Pept. 57:359-370 (1995). The term "peptide" or "oligopeptide," as used herein, embraces all of the foregoing, and also includes biologically active variants of the foregoing.

Likewise, various changes may be made to the oligopeptide including the addition of various side groups which do not affect the manner in which the oligopeptide functions, or which favorably affect the manner in which the oligopeptide functions. Such changes may involve adding or subtracting charge groups, substituting amino acids, adding lipophilic moieties that do not affect biological activity but that affect the overall charge characteristics of the molecule, facilitating drug delivery, etc. Per each such change, no more than routine experimentation is required to test whether the molecule functions according to the invention. One simply makes the desired change or selects the desired peptide and evaluates the peptide for inhibition of the NF-κβ signaling pathway.

The invention also embraces functional variants of the oligopeptides. As used herein, a "functional variant" or "variant" of an isolated peptide is a peptide which contains one or more modifications to the primary amino acid sequence of the peptide and retains the properties disclosed herein. Modifications which create a functional variant of the peptide can be made, for example, 1) to enhance a property of a peptide, such as peptide stability in an expression system; 2) to provide a novel activity or property to the peptide, such as the addition of an antigenic epitope or addition of a detectable moiety; or 3) to provide a different amino acid sequence that produces the same or similar peptide properties. Modifications to a peptide can be made to a nucleic acid which encodes the peptide, and can include deletions, point mutations, truncations, amino acid substitutions and additions of amino acids. Alternatively, modifications can be made directly to the peptide, such as by cleavage, addition of a linker molecule, addition of a detectable moiety, such as biotin, addition of a fatty acid, substitution of one amino acid for another and the like. Modifications also embrace fusion proteins comprising all or part of the oligopeptide amino acid sequence.

If a variant involves a change to an amino acid, then functional variants of the oligopeptide can have either conservative or non-conservative amino acid substitutions. Conservative amino acid substitutions are substitutions which retain a property of the original amino acid such as charge, hydrophobicity, conformation, etc. Examples of conservative substitutions of amino acids include substitutions made amongst amino acids within the following groups: (a) M, I, L, V; (b) F, Y, W; (c) K, R, H; (d) A, G; (e) S, T; (j) Q, N; and (g) E, D.

The peptides described herein are characterized by their ability to inhibit the NF-κβ signaling pathway. Although not wishing to be bound by any particular mechanism of operation, it is believed that the peptides may act upon the NF-κβ signaling pathway by inhibiting the synthesis of the MyD88 coupling protein and its membrane translocation, and possibly and additionally, by increasing the NF-κβ p50/p50 homodimer nuclear translocation and altering heterodimer p65/p50 dynamics. These properties also provide a basis for making and testing variant peptides.

Pharmaceutical compositions including the oligopeptides of this invention are administered to a subject in an effective amount to treat conditions characterized by inflammation or by excessive activation of macrophage or neutrophils. Such conditions include rheumatoid arthritis, lupus and psoriasis. The compositions are administered to a subject in need of such treatment in an amount effective to reduce the effects of the inflammation.

The compositions of this invention can also be administered to a subject to prevent scarring, or to treat the causes of scar formation. Without wishing to be bound by any specific theory or mechanism, scarring is believed to be the result, in part, of a process mediated by leukocytes. The compositions of the invention are believed to inhibit late stage inflammation and scarring by inhibiting the activity and mobility of leukocytes and the recruitment of fibroblasts to the site of a wound. Scarring is also believed to be inhibited as a result of the inhibition of the fibroblast growth factor receptor ("FGFR"), and specifically, by the inhibition of fibroblast growth factor receptor signaling adaptor 3 which is present in man, rats and mice.

The term "subject," as used herein, means a human or non-human mammal, including but not limited to, a dog, cat, horse, cow, pig, sheep, goat, chicken, primate, rat, and mouse.

The terms "prevent" and "preventing" as used herein refer to completely or partially inhibiting a biological response, as well as inhibiting an increase in a biological response.

The oligopeptides may be administered as part of a pharmaceutical composition. Such a pharmaceutical composition may include the peptides in combination with any standard pharmaceutically acceptable carriers which are known in the art. The compositions should be sterile and contain a therapeutically effective amount of the peptides or other therapeutic compound in a unit of weight or volume suitable for administration to a patient. The term "pharmaceutically acceptable" means a non-toxic material that does not interfere with the effectiveness of the biological activity of the active ingredients. The characteristics of the carrier will depend on the route of administration. Pharmaceutically acceptable carriers include diluents, fillers, salts, buffers, stabilizers, solubilizers, and other materials which are well known in the art.

When used therapeutically, the compounds of the invention are administered in therapeutically effective amounts. In general, a therapeutically effective amount means that amount necessary to delay the onset of, inhibit the progression of, or halt altogether the particular condition being treated. Therapeutically effective amounts specifically are those which desirably have an effect on the inflammation, or influence the mobility of leukocytes following an inflammatory event. Generally, a therapeutically effective amount will vary with the subject's age, and condition, as well as the nature and extent of the disease in the subject, all of which can to be determined by one of ordinary skill in the art. The dosage may be adjusted by the individual physician, particularly in the event of any complication. A therapeutically effective amount typically varies from 0.01 mg/kg to about 1000 mg/kg, preferably from about 0.1 mg/kg to about 200 mg/kg and most preferably from about 0.2 mg/kg to about 20 pig/kg, in one or more close administrations daily, for one or more days. The effect of the administered therapeutic composition can be monitored by standard diagnostic procedures.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, xylitol, dextrose and sodium chloride, lactated Ringer's or fixed oils. Intravenous vehicles include fluid and nutrient replenishers, electrolyte replenishers (such as those based on Ringer's dextrose or xylitol), and the like. Preservatives and other additives may also be present such as, for example, antimicrobials, antioxidant, chelating agents, and inert gases, and the like.

The pharmaceutical composition of the invention can be administered by any conventional route, including injection, gradual infusion over time, or oral administration in solid dosage or encapsulated forms. The administration may, for example, be oral, intravenous, intracranial, intraperitoneal, intramuscular, intracavity, intrarespiratory, ocular, oral washes, subcutaneous, or transdermal. The route of administration will depend on the composition of a particular therapeutic preparation of the invention, and in some cases, on the intended site of action. The present compositions can be delivered directly to the site of action.

Other delivery systems can include time-release, delayed release or sustained release delivery systems. Such systems can avoid repeated administrations of the active compounds of the invention, increasing convenience to the subject and the physician. Many types of delayed release delivery systems are available and known to those of ordinary skill in the art. They include polymer-based systems such as polylactic and polyglycolic acid, polyanhydrides and polycaprolactone; nonpolymer systems include lipids such as sterols, and particularly cholesterol, cholesterol esters and fatty acids or neutral fats such as mono-, di and triglycerides; hydrogel release systems; silastic systems; peptide based systems; wax coatings, compressed tablets using conventional binders and excipients, partially fused implants and the like. In addition, pump based hardware delivery systems can be used, some of which are adapted for implantation.

A long-term sustained release implant also may be used. "Long-term" release, as used herein, means that the implant is constructed and arranged to deliver therapeutic levels of the active ingredient for at least 30 days, and preferably 60 days. Long-term sustained release implants are well known to those of ordinary skill in the art and include some of the release systems described above.

The invention also includes cell implants for secreting the oligopeptides or analogues to a site in the body. The cell implant includes the vectors described herein for producing a biologically active peptide. Cell implants can be used effectively for treating inflammatory conditions or for preventing scarring.

EXAMPLE

Inhibition of NF-κβ with MLIF

Synthetic MLIF (Met-Gln-Cys-Asn-Ser; SEQ ID NO:1) was obtained and added to PMA stimulated (induced) and unstimulated (constitutive) U-937 cells (a human monocyte cell line). The control runs lacked MLIF.

The V-937 cells were incubated for 24 hours and 48 hours at 37° C. and under 5% $CO_2$. Nuclear extracts obtained by NaCl hypo/hypertonic shock and freeze-thawing cycles, were processed in 7% polyacrylamide gels by EMSA and read by densitometry. At 24 hours, 44% and 12% of the constitutive and the induced expression, respectively, of NF-κβ translocation was inhibited by MLIF ($p<0.001$). At 48 hours, 25% and 28% of the constitutive and the induced expression, respectively, of NF-κβ translocation was inhibited by MLIF ($p<0.001$). p50/p50 homodimers and p65/p50 heterodimers were found by super-shift analysis of the NF-κβ product. P50/p50 homodimers act as inhibitors, while p65/p50 heterodimers are the leading gene transcriptors.

FIG. 1 is a diagram of the NF-κβ signaling pathway showing the sites of action of MLIF. As shown, MLIF is believed to interact with the membrane-related MyD88 recruitment pathway in monocytes, by inhibiting the synthesis of the MyD88 coupling protein and its membrane translocation, and by increasing the p50/p50 homodimer nuclear translocation and altering heterodimer p65/p50 dynamics. This, in turn, results in the inhibition of pro-inflammatory cytokines IL-1β and IL-6, which are prominent in this signaling pathway. The innate immune response is triggered by pathogen-associated molecular patterns acting upon toll-like receptors (TLR) on the cell membrane. TLR4 responds to LPS of Gram negative bacteria, bringing together TLR4, MD-2 and CD14 in the cell membrane. This complex attracts coupling-protein MyD88-dependent genes (TNFα, IL-1β, IL-6 and IL-8).

Figure 2:
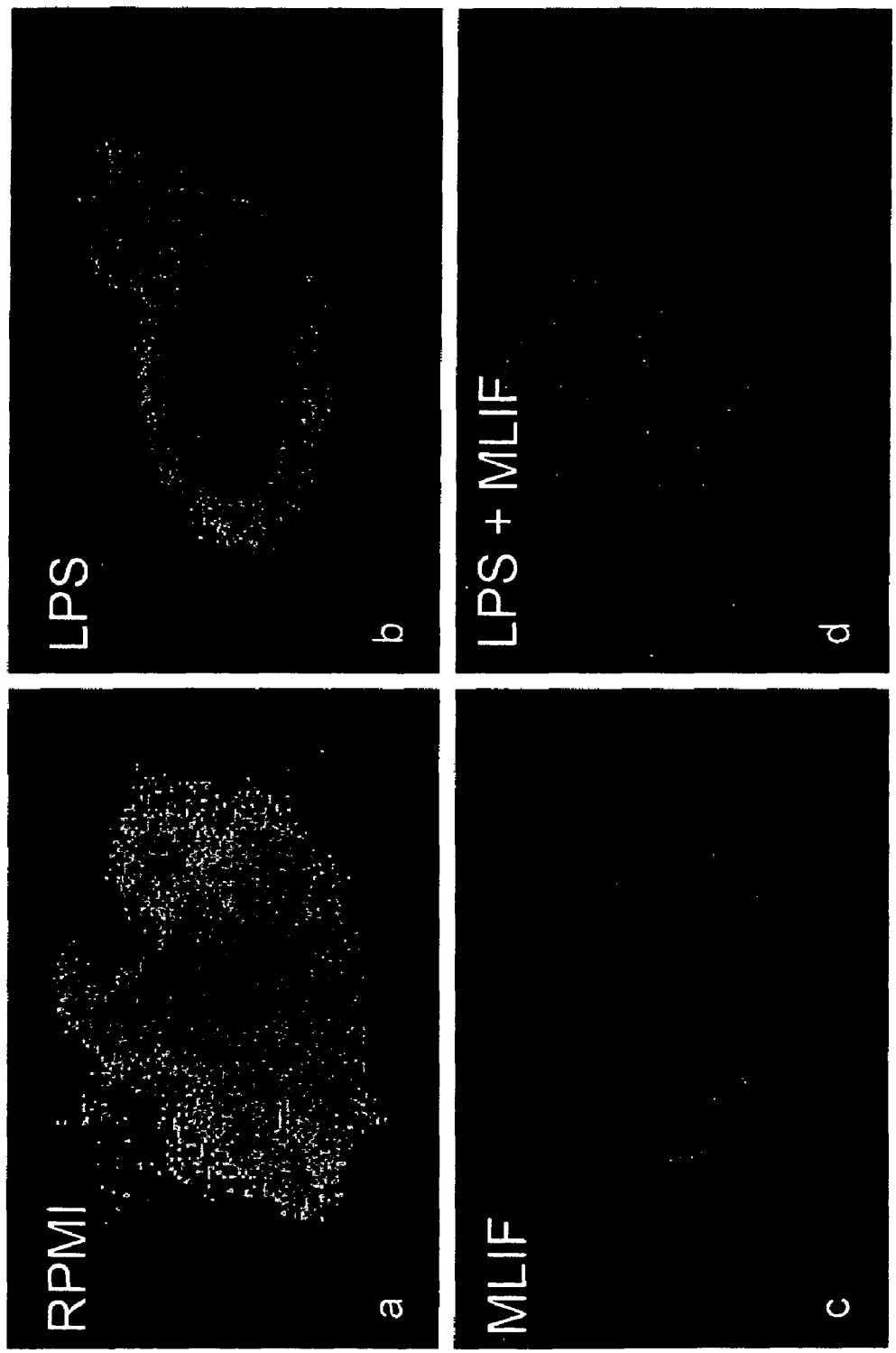
FIG. 2 is a series of confocal scanning microscopy images showing the immunoflourescent staining of U937 cells after 4 hours following exposure to the cytokines and agents shown.

Using real-time PCR, PMA or LPS-stimulated cells reveal only minimal transcription of MyD88 after four hours, reaching normal or minimal over-expression by 24 hours. In contrast, MLIF causes a sudden MyD88 induction at two hours, followed by a steady decrease, without recovery, after 24 hours, and levels substantially below baseline by 48 hours. Confocal microscopy supported these preliminary findings, as shown in FIG. 2. A diminished MyD88 can lead to poor transcription of TNFα, IL-1β, IL-6 and IL-8 genes. Some experiments have shown that MLIF depresses LPS-induced immunoreactive IL-6 and IL-1β. These preliminary results suggest that, unlike cytopenetrating peptides, MLIF may primarily act close to the cell membrane, disrupting the MyD88 bridging of TIR domains, and consequently the downstream IRAK-1→TRAF6→IKKs route toward NF-κβ nucleus translocation.

In some experiments using PBMC, MLIF-like products of other microorganisms induced the expression of IL-10, the prototype anti-inflammatory cytokine, as measured by ELISA.

The origin and striking multiplicity of biological actions of MLIF upon so many cell types, have begun to be understood more precisely through its apparent effect upon membrane MyD88 and down stream NF-κβ translocation, essential steps in obtaining innate immunity.

Those skilled in the art will recognize, or be able to ascertain, using no more than routine experimentation, many equivalents to the specific embodiments of the invention described herein. This invention is not intended to be limited to any specific embodiments or to the examples provided herein which are illustrative only. Equivalents are intended to be encompassed by the following claims.

All references cited herein are incorporated by reference in their entirety.

What is claimed is:

1. An isolated oligopeptide selected from the group consisting of the peptide consisting of Cys-Asn-Ser and the peptide consisting of SEQ ID NO: 1, said oligopeptide being capable of inhibiting the NF-κβ signaling pathway in vitro.

2. The oligopeptide of claim 1 which is the three amino acid peptide Cys-Asn-Ser.

3. A pharmaceutical composition comprising the oligopeptide of claim 1 and suitable adjuvants.

4. A method for inhibiting the NF-κβ signaling pathway in vivo in a subject by administering to the subject an effective amount of the pharmaceutical composition of claim 3.

5. The method of claim 4 wherein the oligopeptide is the Monocyte Locomotion Inhibitory Factor (MLIF).

6. The method of claim 4 wherein the oligopeptide is Cys-Asn-Ser.

7. A method for inhibiting scar formation comprising administering to a subject the pharmaceutical composition of claim 3.

8. The method of claim 7 wherein the oligopeptide is Cys-Asn-Ser.

9. The method of claim 7 wherein the oligopeptide blocks the activity of fibroblast growth factor receptor signaling adaptor.

10. The oligopeptide of claim 1 which is SEQ ID NO: 1.

11. An isolated pentapeptide having the terminal pharmacophore group -Cys-Asn-Ser, wherein the -Ser group is located at a terminal position in said pentapeptide, and wherein said pentapeptide is capable of inhibiting the NF-κβ signaling pathway in vitro.

12. The pentapeptide of claim 11 wherein the first amino acid of said pentapeptide is Met.

* * * * *